(12) United States Patent
Kiselev et al.

(10) Patent No.: US 9,448,167 B2
(45) Date of Patent: Sep. 20, 2016

(54) MEASUREMENT DEVICE AND METHOD FOR DETECTION OF AIRBORNE PARTICLES

(71) Applicant: Université de Genève, Genève (CH)

(72) Inventors: Denis Kiselev, Genève (CH); Luigi Bonacina, Lausanne (CH); Jean-Pierre Wolf, Genève (CH)

(73) Assignee: UNIVERSITE DE GENEVE, Geneva (CH)

( * ) Notice: Subject to any disclaimer, the term of this patent is extended or adjusted under 35 U.S.C. 154(b) by 248 days.

(21) Appl. No.: 13/891,085

(22) Filed: May 9, 2013

(65) Prior Publication Data

US 2013/0301047 A1 Nov. 14, 2013

(30) Foreign Application Priority Data

May 12, 2012 (EP) .................................... 12167800

(51) Int. Cl.
*G01N 15/02* (2006.01)
*G01N 21/47* (2006.01)
(Continued)

(52) U.S. Cl.
CPC .......... *G01N 21/47* (2013.01); *G01N 15/1434* (2013.01); *G01N 15/1459* (2013.01);
(Continued)

(58) Field of Classification Search
CPC ............. G01N 15/12; G01N 15/1245; G01N 15/1456; F21Y 2113/005; G01D 11/28; G09G 3/32
USPC ........................... 356/336, 338, 340–343, 73
See application file for complete search history.

(56) References Cited

U.S. PATENT DOCUMENTS

| 7,127,356 | B2* | 10/2006 | Nicoli | ................ | G01N 15/0227 |
| | | | | | 356/336 |
| 2003/0223063 | A1* | 12/2003 | Hill | ........................ | G01N 21/64 |
| | | | | | 356/340 |

(Continued)

FOREIGN PATENT DOCUMENTS

GB 2 346 445 A 8/2000

OTHER PUBLICATIONS

Pan, Yong-Le, et al., "Dual-excitation-wavelength fluorescence spectra and elastic scattering for differentiation of single airborne pollen and fungal particles," *Atmospheric Environment*, vol. 45, pp. 1555-1563 (2011).

(Continued)

*Primary Examiner* — Kara E Geisel
*Assistant Examiner* — Iyabo S Alli
(74) *Attorney, Agent, or Firm* — Christensen Fonder P.A.

(57) ABSTRACT

A measurement device and method for the detection of airborne particles. The device includes a nozzle designed to produce a laminar flow of air with a flow path beyond the nozzle, a first laser and a second laser being positioned for emitting time-amplitude modulated laser light with intersecting laser beams with a laser beam intersection region in a region of the air flow path, and two photodetectors positioned for the detection of laser light scattered in the laser beam intersection region by airborne particles contained in the laminar air flow. The lasers are designed for emission of time-amplitude modulated laser light of identical laser emission wavelength, and the photodetectors are positioned and designed each for the detection of scattered laser light from both lasers.

14 Claims, 10 Drawing Sheets

(51) Int. Cl.
*G01N 21/64* (2006.01)
*G01N 15/14* (2006.01)
*G01N 15/00* (2006.01)

(52) U.S. Cl.
CPC .......... G01N21/64 (2013.01); G01N 21/6486 (2013.01); *G01N 2015/0038* (2013.01); *G01N 2015/0046* (2013.01); *G01N 2015/1447* (2013.01)

(56) References Cited

U.S. PATENT DOCUMENTS

2004/0125371 A1 7/2004 Chang et al.
2006/0152722 A1* 7/2006 Northby .................. G01P 5/20
356/337

OTHER PUBLICATIONS

Pan, Yong-Le, et al., "Rapid classification of aerosols by single-laser-shot Fluorescence spectra and elastic scattering patterns," *Conference on Lasers and Electro-Optics*, pp. 401-402 (Jun. 6, 2003).

Pan, Yong-Le, et al., "Fluorescence spectra of atmospheric aerosol particles measured using one or two excitation wavelengths: Comparison of classification schemes employing different emission and scattering results," *Optics Express*, vol. 18, No. 12, pp. 12436-12457 (Jun. 7, 2010).

Kiselev, Denis, et al., "Individual bioaerosol particle discrimination by multi-photon excited fluorescence," *Optics Express*, vol. 19, No. 24, pp. 24516-24521 (Nov. 21, 2011).

* cited by examiner

MEASUREMENT DEVICE AND METHOD FOR DETECTION OF AIRBORNE PARTICLES

RELATED APPLICATION

The present application claims priority to European Patent Application No. 12 167 800.7, filed May 12, 2012, the disclosure of which is hereby incorporated by reference herein in its entirety.

FIELD OF THE INVENTION

The present invention pertains to a measurement device for the detection of airborne particles, the device comprising a nozzle designed to produce a laminar flow of air with a flow path beyond the nozzle, a first laser and a second laser, the first laser and the second laser being positioned for emitting laser light with intersecting laser beams with a laser beam intersection region in a region of the air flow path, and a first photodetector and a second photodetector positioned for the detection of laser light scattered in the laser beam intersection region by airborne particles contained in the laminar air flow.

BACKGROUND

In general, the present invention is situated in the context of precaution and/or protection means for detecting hazardous airborne particles. The growing concentration of different types of aerosols in the atmosphere becomes more and more an important issue. Their specific influence on the climate change and air quality is still an open question. More than that, recently new threats like bio-terrorism that employs biological particles as an arm of massive destruction have appeared. Reliable and cost-effective aerosol detectors, fast and with a high discrimination power, are still highly desirable in the market.

Particular species of aerosol particles, like pollens and spores, have a large impact on human health. Some of them are responsible for health problems like allergies affecting, according to statistical analysis, about 20% of the European population. The size of potentially hazardous airborne particles spreads over a range situated approximately between parts of a micrometer and some hundred micrometers.

A variety of different measurement devices and methods for a detection of airborne particles are known, which are mainly based on light scattering measurements for estimating the size of particles contained in an aerosol and, in some cases, detection of the position of the particle at a given moment.

A first known, simplest and in industry still most applied, measurement device and method for this purpose is based on one laser emitting a spatially shaped laser light beam for obtaining an elliptical laser light spot in a measurement region, where an air flow from a nozzle crosses the laser beam, and one photodetector for detecting scattered light from a particle contained in the air flow and crossing the laser beam is provided. An output signal from the photodetector is then used to calculate the particle size.

Another known approach is based on the use of one laser in combination with two photodetectors for acquiring, in different angular orientation with respect to the laser beam, scattering signals from a particle crossing the laser beam.

Because of signal acquisition in two different light scattering angles, this approach allows for a more precise determination of a particle size thanks to simultaneous acquisition of two scattering patterns than the first approach described above. However, this approach is not adequate for a sufficient determination of the exact location of a detected particle.

A further known approach is based on the use of two lasers emitting laser light at different wavelengths in combination with two photodetectors provided with different spectral filters adapted to the two different laser emission wavelengths for acquiring scattered laser light from a particle crossing the laser beams, selectively for the emission wavelengths of the two lasers and central transmission wavelengths of optical band pass filters provided to the photodetectors designed for selective detection of laser light from an assigned laser. However, this approach suffers from limitations in particle size measurement because, for both photodetectors, only scattered light from one laser at a detection wavelength assigned to the related light-emitting laser is detected. Consequently, also this known approach is not adequate for solving imprecisions of particle size determination, particularly because of a potentially chromatically based error, and a correct determination of an actual particle location is also impaired by the inherent disadvantages of this approach.

The solutions according to prior art therefore all suffer from an insufficient precision of a determination of size and location of airborne particles.

SUMMARY

It is the object of the present invention to overcome the above mentioned difficulties and to realize an improved measurement device and measurement method as described in the following.

To this effect, the present invention proposes a measurement device and a measurement method, which are characterized by the features enumerated in claims 1 and 10, respectively, and which allow achievement of the objectives identified above.

The problems associated with known measurement devices and methods as described above are solved, according to the invention, by a measurement device for the detection of airborne particles, the device comprising a nozzle designed to produce a laminar flow of air with a flow path beyond the nozzle, a first laser and a second laser, which are time-amplitude modulated, the first laser and the second laser being positioned for emitting laser light with intersecting laser beams with a laser beam intersection region in a region of the air flow path, and a first photodetector and a second photodetector positioned for the detection of laser light scattered in the laser beam intersection region by airborne particles contained in the laminar air flow.

In particular, the measurement device according to the present invention distinguishes from prior art in that the first and the second laser are designed for emission of laser light of identical laser emission wavelength, and the first photodetector and the second photodetector are positioned and designed each for the detection of scattered laser light from both the first laser and the second laser.

The lasers may be any known light sources capable of emitting coherent laser light, such as gas lasers, solid-state lasers, dye lasers, or laser diodes. "Identical laser emission wavelength" shall mean that the same spectral laser emission line or band is used, or laser diodes similar to one another are used, wherein small wavelength deviations or shifts, which may be in the range of some nanometers, are neglected.

The object of the invention is also solved by a measurement method for the detection of airborne particles by means of a measurement device according to the invention, the measurement device comprising a nozzle designed to produce a laminar flow of air with a flow path beyond the nozzle, a first laser and a second laser which are time-amplitude modulated, the first laser and the second laser being positioned for emitting laser light with intersecting laser beams with a laser beam intersection region in a region of the air flow path, and a first photodetector and a second photodetector positioned for the detection of laser light scattered in the laser beam intersection region by airborne particles contained in the laminar air flow. The measurement method comprises the step of producing by means of the nozzle a laminar flow of air potentially containing airborne particles to be detected. In particular, the measurement method is characterized by the further steps of emitting laser light of identical wavelength from the first and the second laser, and detecting laser light scattered by an airborne particle located in a superposition region of the region of the air flow path with the intersection region of the laser beams from the first laser and the second laser both by the first photodetector and by the second photodetector.

The measurement device and the measurement method according to the invention presents significant advantages over the known approaches discussed above. Each one of the two photodetectors is sensitive for and detects scattered light from both lasers, resulting in four different optical response signals from one detected airborne particle/aerosol particle. As a consequence, the particle size can be determined with a significantly higher precision than with the known approaches, for example by determining a ratio of size values derived from the signals from the two detectors for scattered light from one laser, taken at different angles of light scattering. According to the invention, the same is done concerning the scattering signals generated by the beam of the second laser. Furthermore, using the same emission wavelength for both lasers eliminates chromatic effects on particle size determination, that would have to be expected when using two lasers of different emission wavelengths.

Preferably, the first laser and the second laser are positioned for emission of laser beams intersecting on an angle of approximately 90°. Thereby, "approximately 90°" shall mean that the intersection angle does not deviate more than 20°, preferably not more than 10°, and still more preferred not more than 5° from 90°. This allows for determination of the particle size in two planes nearly perpendicular to one another according to the so-called Mie scattering theory. Two scattering light traces generated by light from a first laser, but taken at different scattering angles, allow for a particle size determination in a plane perpendicular to the optical axis of the first laser beam. Similarly, two scattering light traces generated by light from a second laser, also taken at different scattering angles, allow for a particle size determination in a plane perpendicular to the optical axis of the second laser beam. The first laser beam and the second laser beam being oriented approximately perpendicular to one another, the particle size determination can thus be based on four independent scattering signals in two different planes nearly perpendicular to one another. This further improves the precision of the particle size determination by a favorable choice of the geometrical arrangement.

According to one embodiment of the measurement device according to the invention, the first laser and the second laser are designed for emitting modulated laser light, particularly with a phase shift of approximately 90° between the laser beam of the first laser and the laser beam of the second laser. A "phase shift of approximately 90°" shall mean a phase shift deviating not more than 20°, preferably not more than 10°, and still more preferred not more than 5° from 90°. Thus, the scattering light signals from the two photodetectors can be distinguished with respect to the generating laser beams, and an assignment of the scattering signals to the specific laser beam generating the light scattering is facilitated.

Preferably, the first photodetector and the second photodetector are provided each with a narrow-band optical filter with a central transmission wavelength identical to the laser emission wavelength. Thus, a discrimination between signals of scattered light at the laser emission wavelengths and possible other, potentially disturbing, light signals is facilitated.

According to one embodiment, the measurement device is provided with a calculation and control unit designed for correlation of signals of scattered laser light from the first photodetector and the second photodetector for determination of the size of airborne particles scattering the laser light and preferably also for a determination of the location of detected airborne particles from a known intersection region of the laser beams. Thus, by correlating the four photodetector signals and also the known intersection region of the laser beams, not only the size but also the position of an airborne particle in the air flow path can be precisely determined.

According to a further embodiment, the measurement device is provided with a calculation and control unit designed for controlling an adjustment of laser intensities, particularly by adjusting amplitude of analog laser light modulation. Thus, detector saturations potentially caused by too strong signals of scattered light can be avoided. In fact, for particles larger than about 5 μm, the scattering signal is roughly proportional to the second power of the particle diameter. Thus, detector saturation due to scattering signals from large particles is avoided by adjusting amplitude of analog laser light modulation.

According to another embodiment, the measurement device is provided with an imaging detector, particularly a CCD or CMOS camera, designed and positioned for taking an image of a detected airborne particle after receiving an initiating trigger signal. The additional image enables to recognize shape and surface aspects of the detected particle.

According to a further embodiment, the measurement device is provided with an imaging detector, particularly a CCD or CMOS camera, combined with a diverging lens in an optical reception path designed and positioned for taking an image of an airborne particle, after receiving an initiating trigger signal, for determination of a scattering pattern caused by the airborne particle. Thus, besides information about the particle shape, especially about its symmetry, also about the trace of the particle in the air flow when crossing the two intersecting laser beams can be extracted.

According to a still further embodiment, the measurement device is provided with a flash light source for emitting short-wavelength light, particularly ultra-violet light, designed and positioned for exciting fluorescence or phosphorescence from a detected airborne particle, and with an additional, third photodetector, particularly a multi-anode photomultiplier or an intensified CCD camera, combined with an objective for fluorescence or phosphorescence light collection and a spectrally resolving optical element in an optical reception path for fluorescence or phosphorescence emitted by the airborne particle, designed and positioned for the detection of an optical spectrum of the fluorescence or phosphorescence emitted by the airborne particle. This embodiment allows for a precise identification of the species of the detected airborne particle, as its fluorescence and/or phosphorescence spectrum represents a unique signature disclosing at least the associated family and preferably, also the specific species of the particle itself.

The different embodiments of the measurement method according to the invention present analogous advantages as the embodiments of the measurement device as described above, according to similar specific features.

According to one embodiment of the measurement method, the first laser and the second laser are positioned for emission of laser beams intersecting on an angle of approximately 90°.

Preferably, the first laser and the second laser are operated for emitting modulated laser light, particularly with a phase shift of approximately 90° between the laser beam of the first laser and the laser beam of the second laser.

According to a further embodiment, signals of scattered laser light from the first photodetector and the second photodetector are correlated by a calculation and control unit of the measurement device for determination of the size of airborne particles scattering the laser light, and preferably also for a determination of the location of detected airborne particles from a known intersection region of the laser beams.

Preferably, the laser intensities are controlled by a calculation and control unit of the measurement device, particularly by adjusting amplitude of analog laser light modulation.

According to one embodiment, following an initiating trigger signal, an image of a detected airborne particle is taken by an imaging detector, particularly a CCD or CMOS camera.

According to a further embodiment, following an initiating trigger signal, an image of a detected airborne particle is taken by an imaging detector, particularly a CCD or CMOS camera, combined with a diverging lens in an optical reception path designed and positioned for taking an image of an airborne particle, after receiving an initiating trigger signal, for determination of a scattering pattern caused by the airborne particle.

According to still a further embodiment of the measurement method according to the invention, following an initiating trigger signal, detected airborne particles capable of fluorescence and/or phosphorescence are excited by a light of short, particularly ultra-violet, wavelength from a flash light source for emission of fluorescence and/or phosphorescence, and emitted fluorescence and/or phosphorescence is detected by a third photodetector, particularly a multi-anode photomultiplier or an intensified CCD camera, combined with an objective collecting the emitted fluorescence and/or phosphorescence, and spectrally resolved by a spectrally resolving element for projection on a photo-sensitive element of the third photodetector for generating an optical spectrum of the fluorescence and/or phosphorescence from the airborne particle.

A subject of the invention is also the use of a measurement device according to one of the related embodiments described above and/or the application of a measurement method according to one of the related embodiments described above for determination of size and/or location, as well as identification, of particles in a gas.

Other features and advantages of the present invention are mentioned in the dependent claims as well as in the description disclosing in the following, particularly with reference to the figures, the invention in more detail.

BRIEF DESCRIPTION OF THE DRAWINGS

The attached figures exemplarily and schematically illustrate the principles as well as several embodiments of the present invention.

FIG. 5a shows schematically in a side view and a top view a first embodiment of a measurement device according to the invention and FIG. 5b illustrates schematically the time evolution of laser emission intensities and detector signals for the measurement device of FIG. 5a.

FIG. 7a shows schematically in a side view and a top view a further embodiment of a measurement device according to the invention and FIG. 7b illustrates schematically the time evolution of laser emission intensities and detector signals, as well as signals for a camera shutter control, for the measurement device of FIG. 7a.

FIG. 8a shows schematically in a side view and a top view a further embodiment of a measurement device according to the invention and FIG. 8b illustrates schematically the time evolution of laser emission intensities and detector signals, as well as signals for a camera shutter control, for the measurement device of FIG. 8a.

FIG. 9a shows schematically in a side view and a top view a further embodiment of a measurement device according to the invention and FIG. 9b illustrates schematically the time evolution of laser emission intensities and detector signals, as well as an emission light intensity of a flash light source and a signal from a further detector, for the measurement device of FIG. 9a.

FIG. 10a shows schematically in a side view and a top view a further embodiment of a measurement device according to the invention, exemplarily as a combination of the measurement device configurations of FIG. 7a and FIG. 9a, and FIG. 10b illustrates schematically the time evolution of laser emission intensities and detector signals, as well as signals for a camera shutter control and an emission light intensity of a flash light source and a signal from a further detector, for the measurement device of FIG. 10a.

DETAILED DESCRIPTION

In the following, the invention shall be described in detail with reference to the above mentioned figures.

Figure 1:
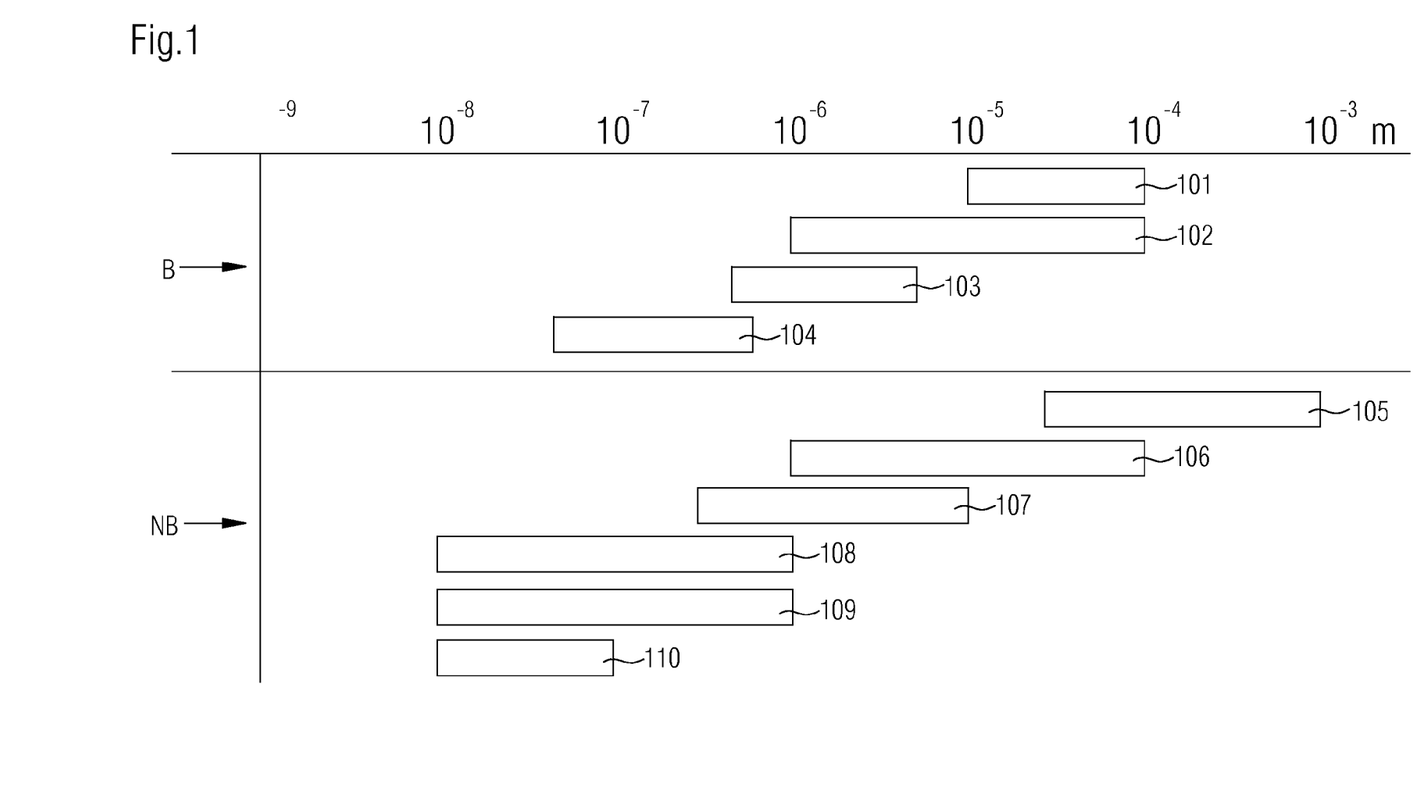
FIG. 1 shows a diagram with typical sizes of biological and non-biological airborne particles.

FIG. 1 shows a diagram with typical sizes of airborne particles. The diagram is divided into an upper part concerning biological air-borne particles B and non-biological air-borne particles NB. Among the biological particles B pollens 101 have the largest size, typically between 10 μm and 100 µm. Spores 102 range between 1 µm and 100 µm, bacteria 103 between about 0.5 µm and 5 µm, and viruses 104 between 50 nm and about 1 µm.

In general, the total size distribution of the group of non-biological airborne particles NB is larger, between 10 nm and 1 mm. The largest ones are so-called "heavy" particles 105 with a size between roughly 50 µm and 1 mm. Ash particles 106 typically have a size between 1 µm and 100 µm, oil smoke particles 107 between 0.5 µm and 10 µm, so-called "nanoparticles" 108 between 10 nm and 1 µm, similar to typical sizes of smog particles 109. Finally, soot particles 110 typically have a size between 10 nm and 100 nm.

Given this situation, the device and the measurement method according to the present invention aim to realize a real-time detection of individual aerosols in the size range of approximately 1 µm to 100 µm, which includes in particular all pollens and spores, some bacteria, virus clusters, as well as ash and oil smoke particles and thus allows to cover a very large range of different aerosols.

Figure 2A:
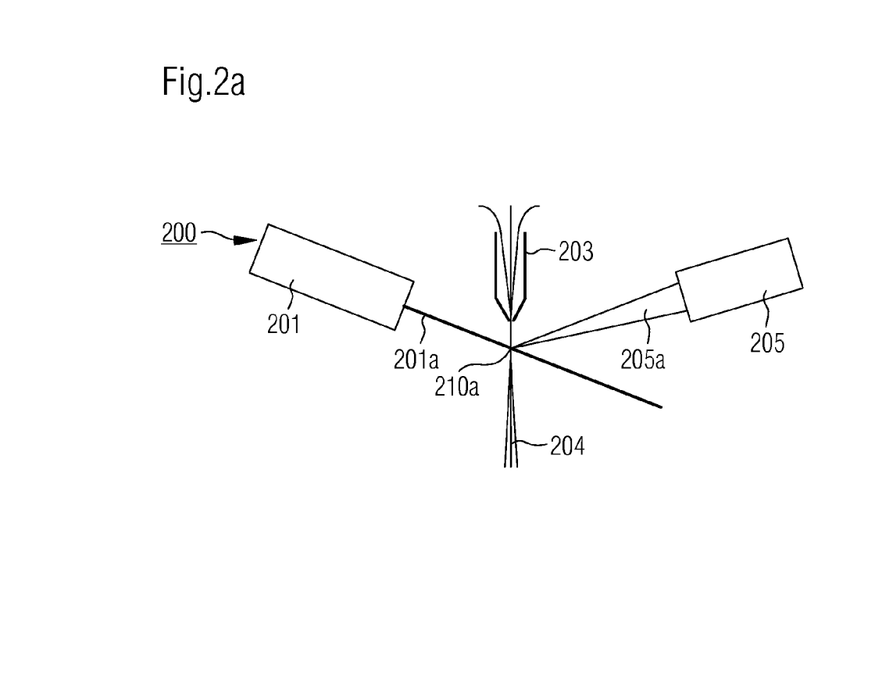
FIGS. 2a and 2b illustrate a known measurement device and method for detecting airborne particles using one laser and one photodetector.
Figure 2B:
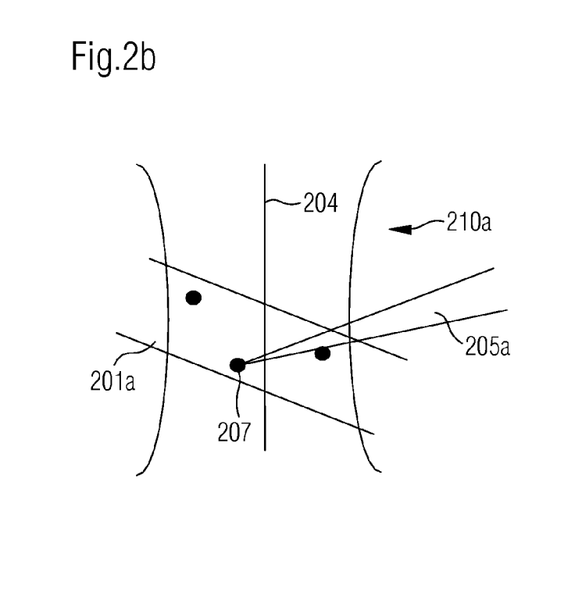

FIGS. 2a and 2b illustrate a known measurement device 200 and a related method for detecting airborne particles 207, using one laser 201 and one photodetector 205. A laser beam 201a emitted from the laser 201 strikes a flow path 204 of laminar flow of air produced by a nozzle 203 in a region 210a of the flow path 204. Laser light scattered by a particle 207 in the air flow path 204 and hit by the laser beam 201a is detected by the photodetector 205, which has a spatial detection range 205a. FIG. 2b shows the region 210a in an enlargement.

This arrangement may be regarded as the simplest one for a detection of aerosol particles and is still most used in aerosol science and industry. Every particle crossing the laser beam 201a will scatter the laser light, and a small part 205a of the scattered light will then be detected by the photodetector 205. An output signal of the detector 205 may then be used for a determination of the particle size. However, this approach is only adequate for a determination of the particle position and size with a precision close to the size of the laser spot.

Figure 3A:
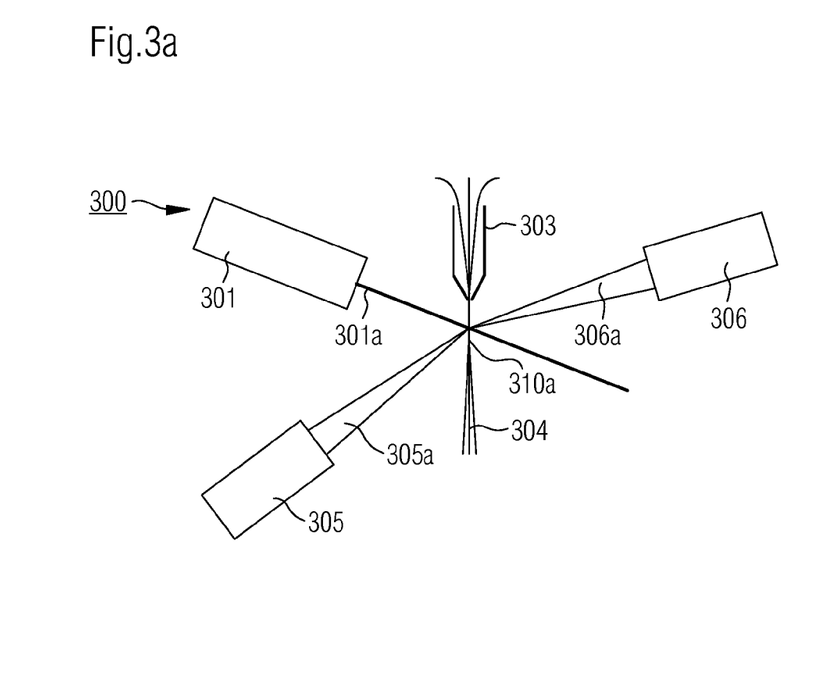
FIGS. 3a and 3b illustrate a known measurement device and method for detecting airborne particles using one laser and two photodetectors.
Figure 3B:
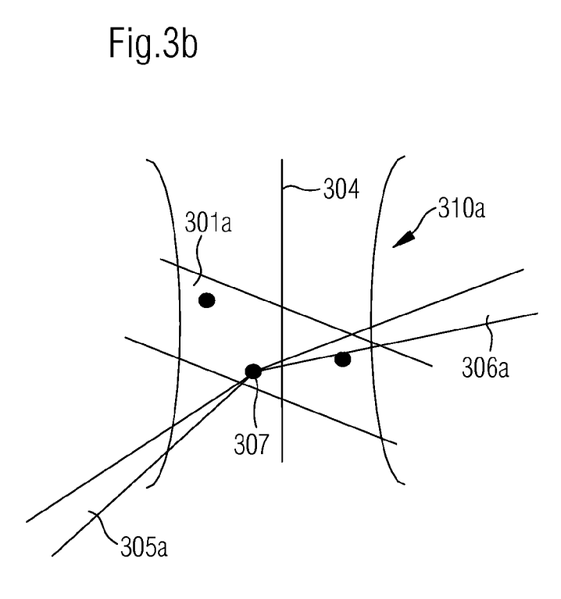

FIGS. 3a and 3b illustrate another known measurement device 300 and a related method for detecting airborne particles 307, using one laser 301 and two photodetectors 305, 306. A laser beam 301a emitted from the laser 301 strikes a flow path 304 of laminar flow of air produced by a nozzle 303 in a region 310a of the flow path 304. Laser light scattered in a first scattering direction by a particle 307 in the air flow path 304 and hit by the laser beam 301a is detected by a first photodetector 305, which has a spatial detection range 305a. Laser light scattered in a second scattering direction by the particle 307 is detected by a second photodetector 306, which has a spatial detection range 306a. FIG. 3b shows the region 310a in an enlargement.

This second known method allows for a particle size determination with a higher precision than the method according to FIGS. 2a and 2b. This second method employs two scattering angles for detection of light scattered by one particle, what makes this measurement independent of the absolute laser intensity. It is adequate for delivering more precise size determinations for spherical particles. However, based on scattering of light from only one laser 301, a localization of a detected particle is very approximate, also when applying this method, and no additional information can be obtained on it. Consequently, this method, as well as the first method illustrated by FIGS. 2a and 2b, is not convenient when to be used in conjunction with other measurements that require knowledge of the exact position of the particle, like particle imaging.

Figure 4A:
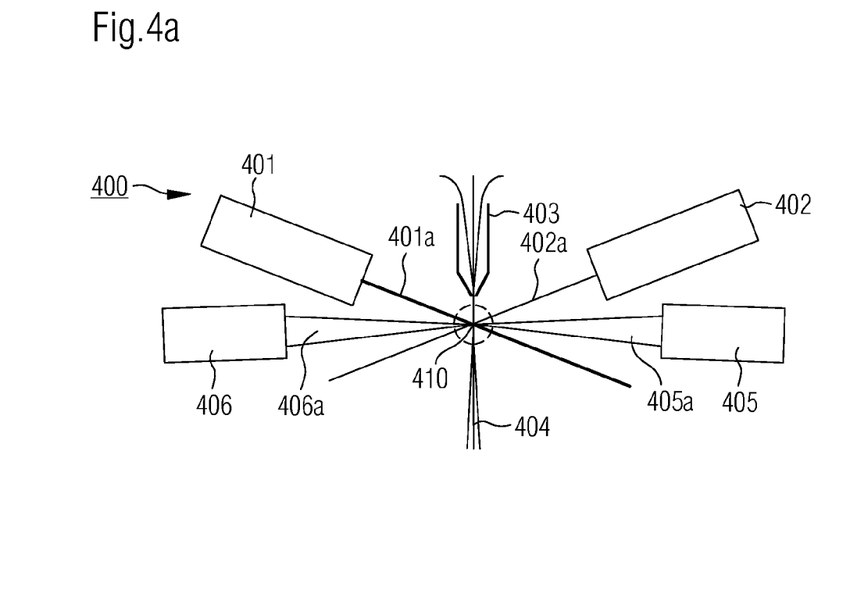
FIGS. 4a and 4b illustrate a known measurement device and method for detecting airborne particles using two lasers emitting laser light at different wavelengths and two photodetectors.
Figure 4B:
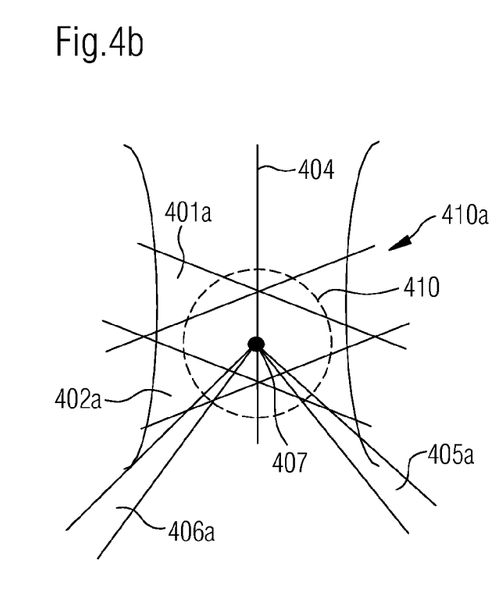

FIGS. 4a and 4b illustrate another known measurement device 400 and a related method for detecting airborne particles 407, using two lasers 401, 402 and two photodetectors 405, 406. The first laser 401 emits a laser beam 401a at a first wavelength, and the second laser 402 emits a laser beam 402a at a second wavelength which is different from the wavelength of the first laser beam 401a. The laser beams 401a, 402a intersect in a region 410. The lasers 401 and 402 with the related laser beam intersection region 410 are positioned in such a way that the intersection region 410 is located in a region 410a of an air flow path 404 of a laminar flow of air generated by a nozzle 403. The first photodetector 405, with a spatial detection range 405a, is provided with a spectral filter for detecting selectively scattered light at the emission wavelength of the first laser 401, and the second photodetector 406, with a spatial detection range 406a, is provided with a spectral filter for detecting selectively scattered light at the emission wavelength of the second laser 402.

Referring particularly to FIG. 4b showing an enlargement of the intersection region 410a, a localization of a particle 407 in the region 410a of the air flow path 404 occurs only when it crosses the laser beam intersection region 410, so that it generates scattered light at the emission wavelengths of both lasers 401, 402, to be selectively detected by the two photodetectors 405, 406.

This approach is adequate for delivering a good localization of a detected particle and, therefore, useful for a combination with other measurement methods relying on a precise particle localization, like particle imaging. However, this method suffers from non-precise particle size determination, because for detection of scattered light from one laser only one photodetector assigned to this laser is used, and the differences between the two laser emission wavelengths and the related detection wavelengths will additionally lead to chromatically induced differences in size determination.

Figure 5A:
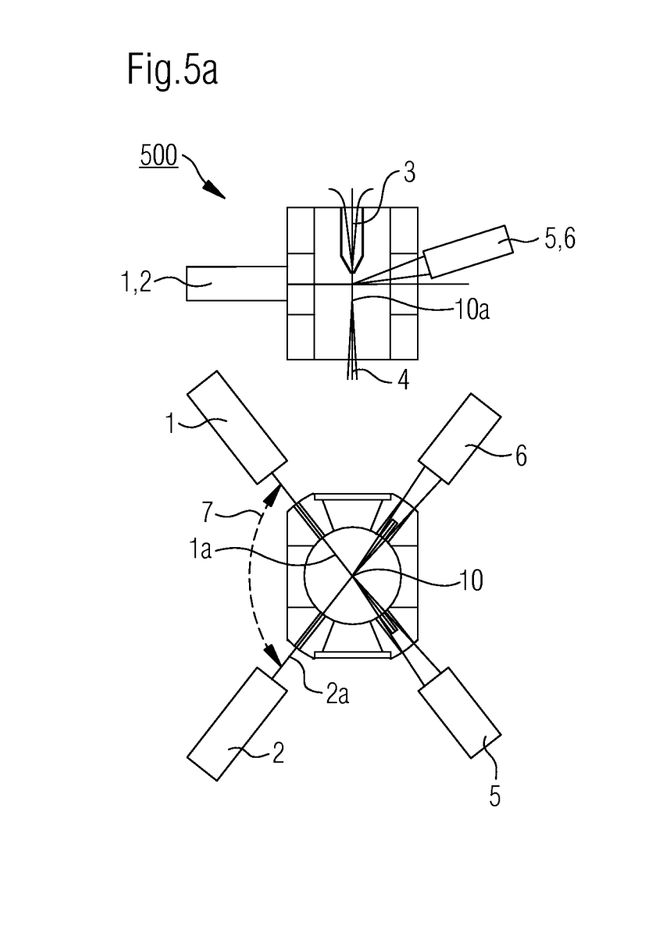

FIG. 5a shows schematically in a side view, in an upper part, and a top view, in a lower part of FIG. 5a, a measurement device 500 according to the invention. The measurement device 500 comprises a nozzle 3 designed to produce a laminar flow of air with a flow path 4 beyond the nozzle 3, a first laser 1 and a second laser 2, the first laser 1 and the second laser 2 being positioned for emitting laser light with intersecting laser beams 1a, 2a with a laser beam intersection region 10 in a region 10a of the air flow path 4, and a first photodetector 5 and a second photodetector 6 positioned for the detection of laser light scattered in the laser beam intersection region 10 by airborne particles contained in the laminar air flow. The first laser 1 and the second laser 2 are designed for emission of laser light of identical laser emission wavelength, and the first photodetector 5 and the second photodetector 6 are positioned and designed each for the detection of scattered laser light from both the first laser 1 and the second laser 2. Preferably, the two lasers 1, 2 are positioned for emission of associated laser beams 1a, 2a intersecting on an angle 7 of approximately 90°.

The lasers 1, 2 may be any known light sources capable of emitting coherent laser light, such as gas lasers, solid-state lasers, dye lasers or laser diodes. "Identical laser emission wavelength" shall mean that the same spectral laser emission line or band is used, or laser diodes similar to one another are used, wherein small wavelength deviations or shifts, which may be in the range of some nanometers, are neglected.

According to one embodiment of the invention, the photodetectors 5 and 6 are provided with narrow-band optical filters with a transmission wavelength identical to the laser emission wavelength, thus allowing for suppression of disturbing signals not originating from scattered laser light from particles to be detected.

The measurement device 500 and the related measurement method according to the invention present significant advantages over the known approaches discussed above. Each one of the two photodetectors 5, 6 is sensitive for and detects scattered light from both lasers 1, 2, resulting in four different optical response signals from one detected airborne particle. The photodetectors 5 and 6 are positioned at a small angle in a forward or backward direction with respect to one of the laser beams 1a, 2a, for example at angles between about 0° to 30°, preferentially between 10° to 25° and most preferably at about 20°. As a consequence, the particle size can be determined with a significantly higher precision than with the known approaches, for example by determining a ratio of size values derived from the signals from the two photodetectors 5, 6 for scattered light from lasers 1, 2, taken at different angles of light scattering. Furthermore, using the same emission wavelength for both lasers 1 and 2 eliminates chromatic effects on particle size determination, that would have to be expected when using two lasers of different emission wavelengths.

The positioning of the two lasers 1 and 2 for generating laser beams intersecting at an angle of approximately 90° allows for determination of the particle size in two planes nearly perpendicular to one another. Two scattering light traces generated by light from the first laser 1, but taken at different scattering angles, allow for a particle size determination in a plane perpendicular to the optical axis of the first laser beam 1a. Similarly, two scattering light traces generated by light from the second laser 2, also taken at different scattering angles, allow for a particle size determination in a plane perpendicular to the optical axis of the second laser beam 2a. The first laser beam 1a and the second laser beam 2a being oriented approximately perpendicular to one another, the particle size determination can thus be based on four independent scattering signals in two different planes nearly perpendicular to one another. Such favorable choice of the geometrical arrangement of the light sources and light detectors used further improves the precision of the particle size determination.

Figure 5B:
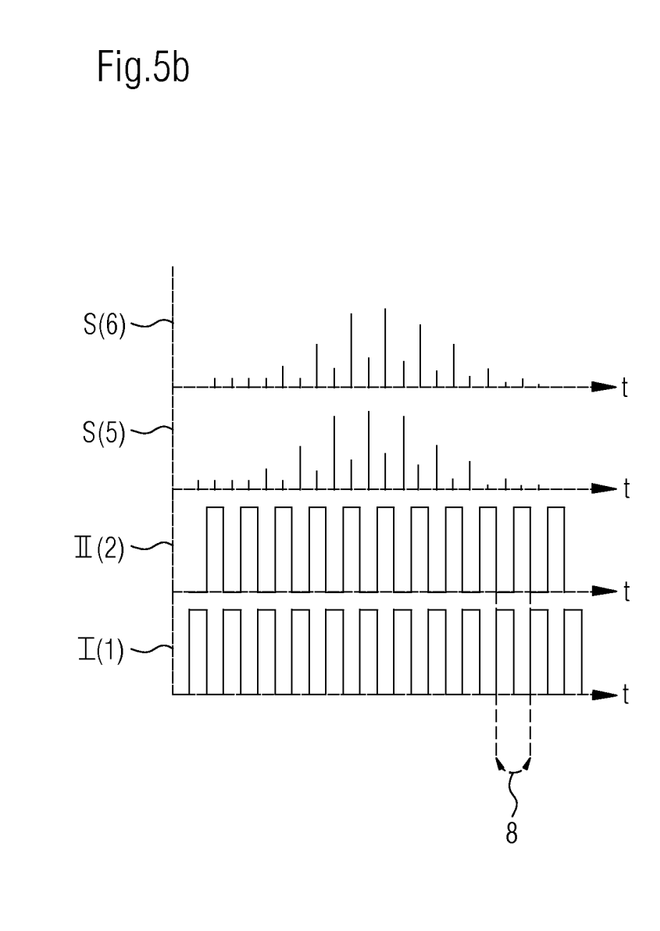

FIG. 5b illustrates schematically the time evolution of laser emission intensities I(1), I(2) and detector signals S(5), S(6) when performing the measurement method according to the invention with the measurement device 500 of FIG. 5a. The two laser beams 1a and 2a are modulated at a high frequency, typically in the MHz range, with a phase shift 8 of approximately 90° between the laser beam 1a from the first laser 1 and the laser beam 2a from the second laser 2, as illustrated in FIG. 5b in a schematic representation of the laser intensity I(1) of the first laser 1 and the laser intensity I(2) of the second laser as a function of time t. The lasers are modulated for emission of modulated light with phase difference 8 of approximately 90°. Thus, at each moment, only one of the two lasers 1, 2 is actively emitting laser light. The frequency modulation of the two laser beams 1a and 2a is preferably done by using frequencies in the range of approximately 0.1 MHz to a few 100 MHz, more preferably in the range of 1 MHz to 100 MHz. Typical cross sections of the laser beams 1a, 2a of the lasers 1, 2 used for the present invention are situated in a range of approximately several μm to a few mm. Due to the fact that the velocity of particles to be determined in the air flow path 4 depends on many parameters, like geometry of the nozzle 3, size and shape of the particle, etc cross sections and modulation frequencies of the lasers beams 1a and 2a are preferably chosen/adjusted in such a way that a particle to be detected will take at least the time of several laser light modulation periods, e.g. three to ten periods and preferably five periods, for its travelling path when crossing the laser beams 1a, 2a. The photodetectors 5 and 6 deliver related signals S(5) and S(6) which are, for the detection of scattered light from one individual laser 1 or 2, different from one another in intensity because of the different spatial orientation of the two photodetectors 1 and 2. For this reason, frequency modulation of the two laser beams 1a and 2a is preferentially used to facilitate distinguishing the source of the scattered light detected in the two photodetectors 5, 6, but is not obligatorily required since such distinction may also be realised by applying an adequate discrimination on the intensity of the collected scattering light at the two photodetectors 5, 6.

Figure 6:
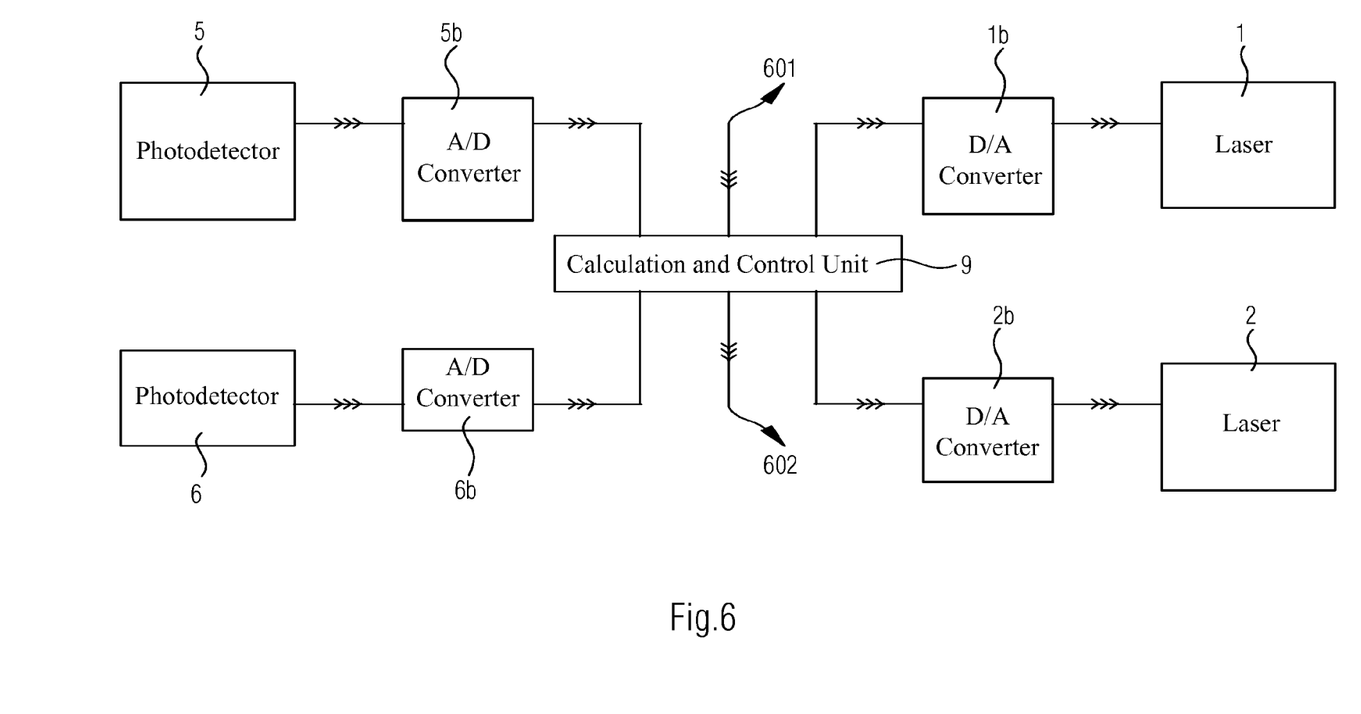
FIG. 6 shows a sketch illustrating the control of laser power adjustment and detector control by a calculation and control unit provided to the measurement device according to the invention.

FIG. 6 shows a sketch illustrating the control of power/intensity adjustment for the lasers 1, 2 and control of the detectors 5, 6 by a calculation and control unit 9 provided to the measurement device 500 of FIG. 5a. Besides that, the calculation and control unit 9 is dedicated for, additionally, correlation of signals of scattered laser light from the first photo first photodetector 5 and the second photodetector 6 for determination of a size of airborne particles scattering the laser light and preferably also for a determination of a location of detected airborne particles from a known intersection region 10 of the laser beams 1a, 2a.

For particles larger than 5 μm, the intensity of scattered light being proportional to the second power of the particle diameter, a detector saturation may occur in case of detecting scattering signals from large particles. In order to avoid such detector saturation, the calculation and control unit 9 is designed for controlling an adjustment of laser intensities, particularly by adjusting amplitude of analog laser light.

The principle of the adjustment of laser power/intensity is as follows: The calculation and control unit 9 receives, triggered by a system clock 601, signals from the photodetectors 5 and 6, processed by fast analog to digital converters 5b and 6b. As a response, in case of a pre-determined threshold intensity indicating a potential detector saturation, the calculation and control unit 9 sends control signals, via fast digital to analog converters 1b and 2b, to the lasers 1 and/or 2 for an adjustment of laser power/intensity to be emitted.

Figure 7A:
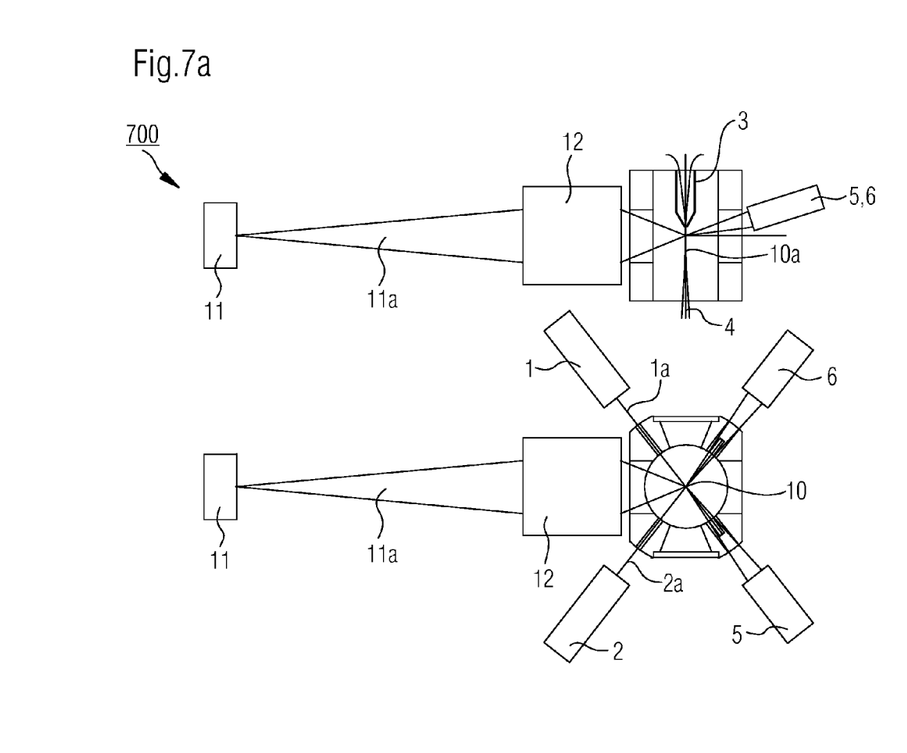

FIG. 7a shows schematically in a side view and a top view a further embodiment of a measurement device 700 according to the invention. The measurement device 700, comprising the basic configuration of the measurement device 500 of FIG. 5a, is provided with an imaging detector 11, particularly a CCD or CMOS camera, designed and positioned for taking an image of a detected airborne particle after receiving an initiating trigger signal. The imaging detector is provided with a camera shutter and a long working distance objective 12 for taking an image of the region 10a and focusing a taken image in an imaging light path 11a on a sensor of the imaging detector 11, when a particle in the air flow path 4 has been detected.

Figure 7B:
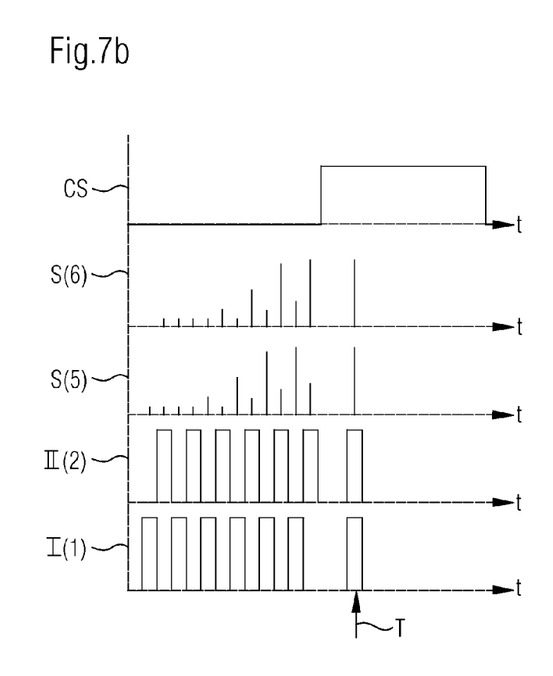

FIG. 7b illustrates schematically the time evolution of laser emission intensities I(1), I(2) and detector signals S(5), S(6) when performing the measurement method according to the invention with the measurement device 700 of FIG. 7a, as well as signals CS for a camera shutter control.

According to this embodiment of the invention, which is enabled by the capability for precise localization of a particle, the two lasers 1 and 2 are initially modulated for alternating laser emission (see intensity traces I(1) and I(2)), until a particle is detected. Then both lasers 1 and 2 are shut off, and a trigger signal is sent to the imaging detector 11 for opening the camera shutter CS in order to start image collection/integration on all pixels for a pre-defined period of time. This is followed at a time T by initiating a short laser flash to be emitted from both lasers 1 and 2 simultaneously. This should be the shortest flash time possible for the applied type of laser and should not exceed 100 ns. The taken image may be used for determining the shape and also specific surface aspects of the detected particle.

Figure 8A:
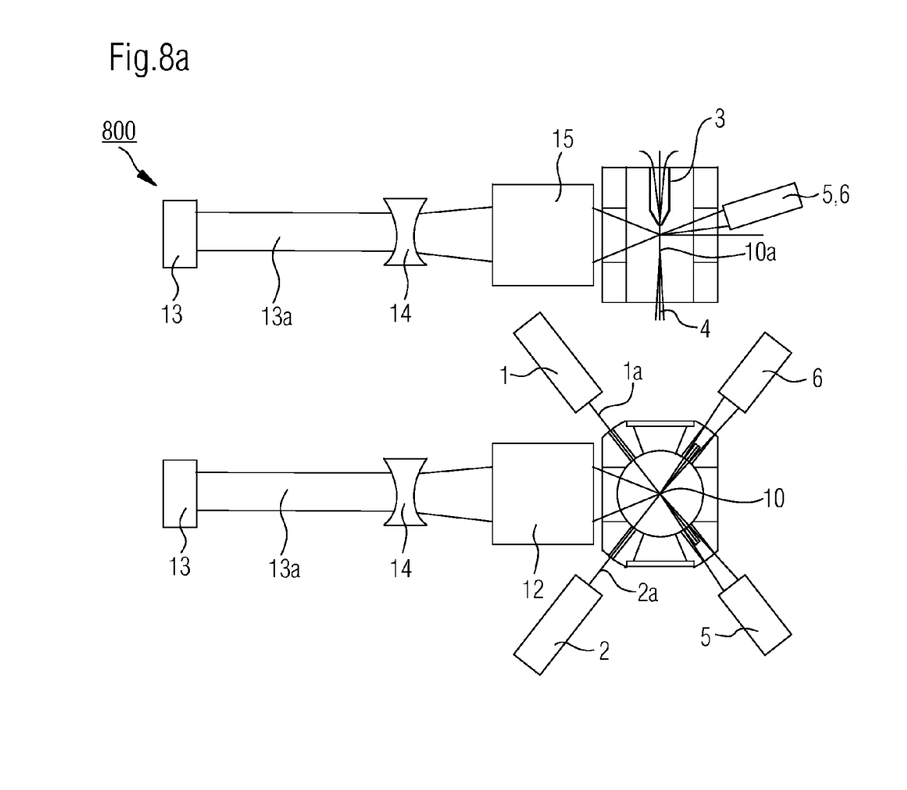

FIG. 8a shows schematically in a side view and a top view a further embodiment of a measurement device 800 according to the invention. The configuration of the measurement device 800 resembles the one of measurement device 700 illustrated by FIG. 7a, except for the fact that the imaging detector 11 of FIG. 7a is replaced by another imaging detector 13 combined with a diverging lens 14 and an objective 15 in an optical reception path 13a. The imaging detector 13 may particularly be a CCD or CMOS camera, provided with a camera shutter.

Figure 8B:
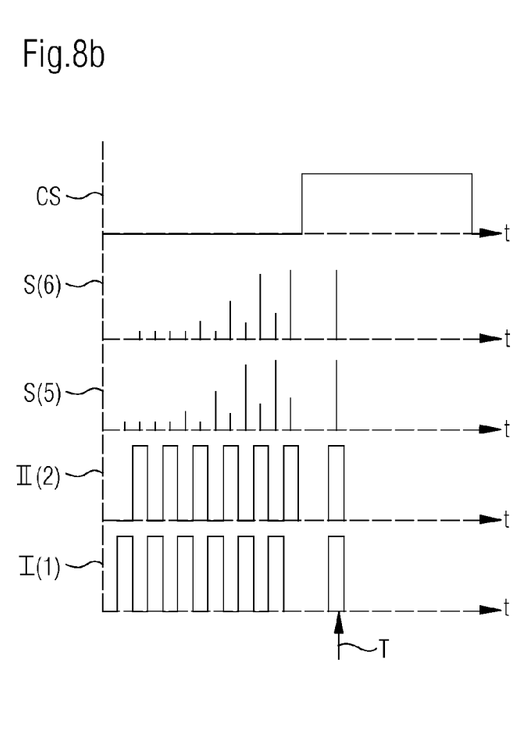

FIG. 8b, resembling the illustration by FIG. 7b, shows schematically the time evolution of laser emission intensities I(1), I(2) and detector signals S(5), S(6), as well as signals CS for a camera shutter control, for the measurement device 800 of FIG. 8a.

Also according to this embodiment of the invention, the two lasers 1 and 2 are initially modulated for alternating laser emission (see intensity traces I(1) and I(2)), until a particle is detected. Then both lasers 1 and 2 are shut off, and a trigger signal is sent to the imaging detector 13 for opening the camera shutter CS in order to start image collection/integration for a predefined period of time and in a way that the camera sensor is completely filled out by a detection light beam 13a resized by the diverging lens 14. The opening of the camera shutter is followed at a time T by initiating a short laser flash to be emitted from both lasers 1 and 2 simultaneously, as described above referring to FIG. 7a.

This approach is particularly useful for determination of an on-fly scattering pattern for a detected airborne particle. Besides information about the particle shape, especially about its symmetry, also information about the trace of the particle in the air flow when crossing the two intersecting laser beams 1a, 2a can be extracted. This approach is not associated with size limitations (concerning the related detection region) like particle imaging, but it is more difficult to extract the information about the particle shape.

Figure 9A:
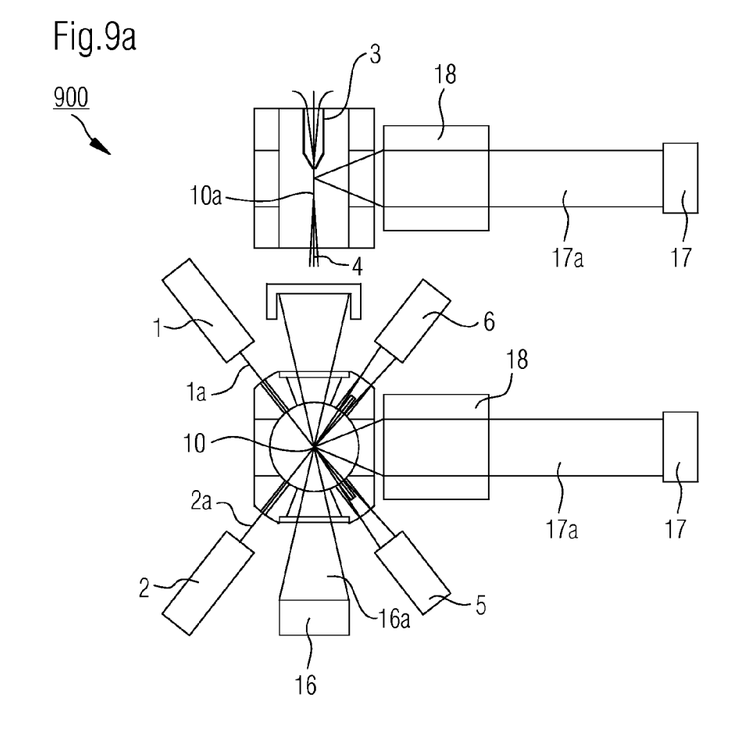

FIG. 9a shows schematically in a side view and a top view a further embodiment of a measurement device 900 according to the invention. The measurement device 900 comprises the basic configuration of the measurement device 500 of FIG. 5a. Additionally, the measurement device 900 is provided with a flash light source 16 for emitting in an emission light beam 16a short-wavelength light, particularly ultraviolet light. The flash light source 16 is designed and positioned for exciting fluorescence and/or phosphorescence from a detected airborne particle. The flash light source may be, for example, a UV laser or a Xenon flash lamp. Furthermore, an additional, third photodetector 17, particularly a multi-anode photomultiplier or an intensified CCD camera, is provided, combined with an objective 18 for fluorescence and/or phosphorescence light collection and a spectrally resolving optical element (not shown) in an optical reception path 17a for fluorescence or phosphorescence emitted by the airborne particle, designed and positioned for the detection of an optical spectrum of the fluorescence or phosphorescence emitted by the airborne particle.

Figure 9B:
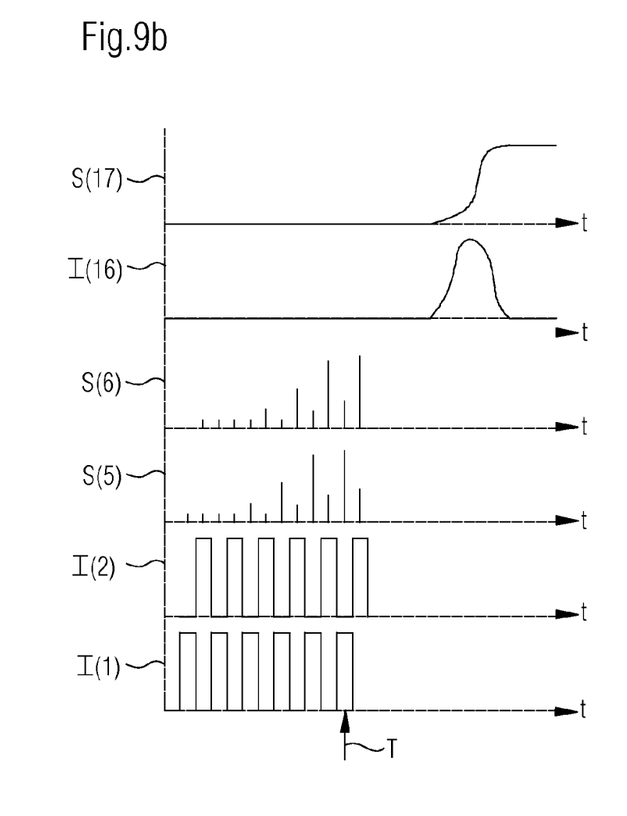

FIG. 9b illustrates schematically the time evolution of laser emission intensities I(1), I(2) and detector signals S(5), S(6), as well as an emission light intensity I(16) of a flash light source 16 and a signal S(17) from a further detector 17, for the measurement device 900 of FIG. 9a.

As for the embodiments described above with reference to FIGS. 5a, 5b, 7a, 7b, 8a, and 8b, the two lasers 1 and 2 are initially modulated for alternating laser emission (see intensity traces I(1) and I(2)), until a particle is detected. Then both lasers 1 and 2 are shut off, and a trigger signal is sent to the flash light source 16 for initiating emission of a light pulse. A prerequisite for this approach is, besides matching an adequate region in the absorption spectrum of the detected particle by the emitted light from the flash light source 16, that the detected particle to be further analysed, based on this approach, is capable at being excited for emission of fluorescence and/or phosphorescence. This precondition is fulfilled for all biological particles and some non-biological particles. A resulting fluorescence and/or phosphorescence signal from the particle is collected by a long distance working objective 18 with infinite back-focal length. The collected emission light from the particle is dispersed by a spectrally resolving optical element (not shown), like a prism or a diffraction grating. The acquired, spectrally resolved, emission light from the particle is then directed to the third detector 17, which should be a highly sensitive multi-pixel detector, particularly a multi-anode photomultiplier or an intensified CCD camera.

This embodiment allows, additionally to particle size and localization determination, for a precise identification of the species of a detected airborne particle, as its fluorescence and/or phosphorescence spectrum represents a unique signature disclosing at least the associated family and preferably, also the specific species of the particle itself.

Figure 10A:
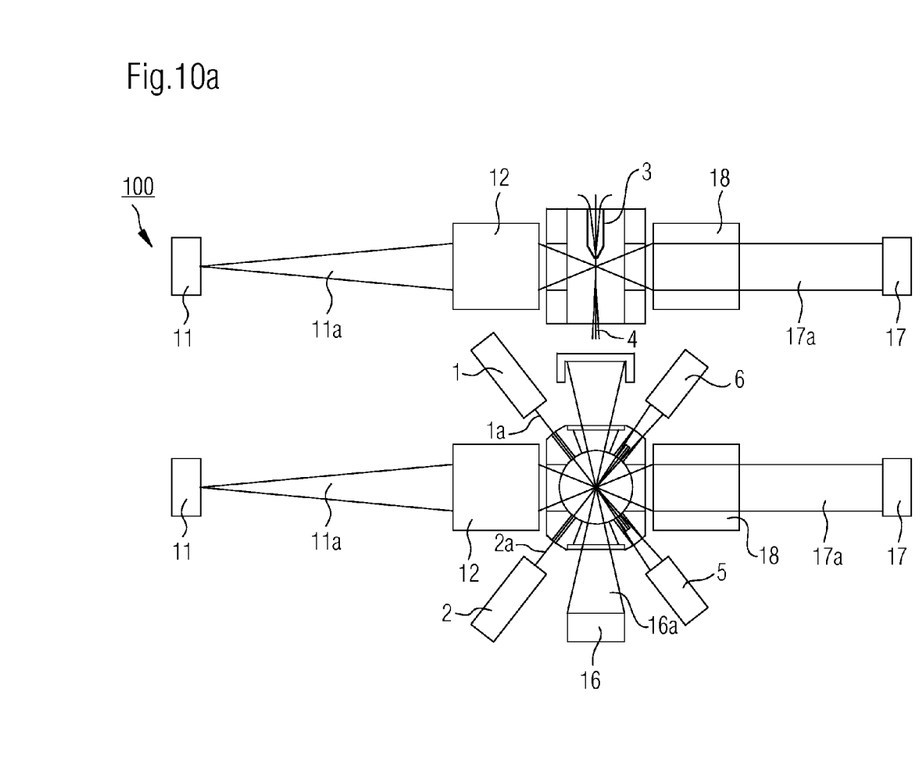

FIG. 10a shows schematically in a side view and a top view a further embodiment of a measurement device 100 according to the invention, the embodiment shown as an example out of several possibilities being a combination of the measurement device configurations 700 and 900 of FIG. 7a and FIG. 9a.

Figure 10B:
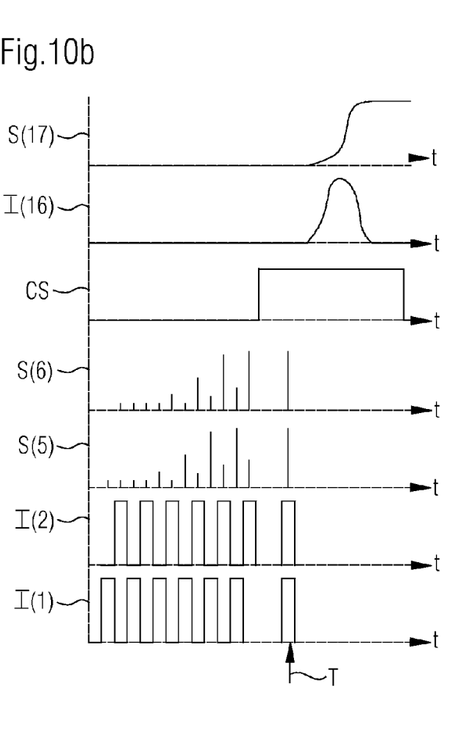

FIG. 10b illustrates schematically the time evolution of laser emission intensities I(1), I(2) and detector signals S(5), S(6), as well as signals CS for a camera shutter control and an emission light intensity I(16) of a flash light source 16 and a signal S(17) from a further detector 17, for the measurement device 100 of FIG. 10a.

This approach is characterized by the highest particle identification power. It combines size measurement, localization, on-fly-imaging and fluorescence and/or phosphorescence acquisition for one and the same detected particle. This approach is particularly useful for determination of particles with a size larger than 10 µm. Consequently, this approach offers, for example, an ideal method for individual pollen identification and counting in real-time.

Finally, the present invention is also related to the use of a measurement device according to one of the related embodiments described above and/or the application of a measurement method according to one of the related embodiments described above for determination of size and/or location, as well as identification, of particles in a gas.

All disclosed embodiments of the invention can be combined with one another, if not explicitly stated otherwise.

In light of the above description of the structure and of the operating mode of the present invention, its advantages are clear. Primarily, the invention enables a precise determination of the size and the location of airborne particles, particularly by use of two time-amplitude modulated lasers and two photodetectors for detecting scattering signals of light from both lasers, the lasers being positioned for light emission in two approximately perpendicular planes, thus allowing the correlation/use of four signals for one detected particle; avoiding any chromatic effect on the particle size determination, as two lasers of identical emission wavelength are used; a precise localisation of a detected particle based on a known intersection point of the two laser beams; and further acquisition of information relating to particle structure and particle identification, particularly enabled by the precise particle localization.

The invention is particularly useful for real-time detection and/or determination of airborne particles with a refractive index different from the one of air, especially for detection and/or determination of pollens, spores, some bacteria, virus clusters, ash and oil smoke particles, as well as soot aggregates.

The invention claimed is:

1. A measurement device for the detection of airborne particles, the measurement device comprising:
 a nozzle designed to produce a laminar flow of air with a flow path, beyond the nozzle,
 a first laser and a second laser, the first laser and the second laser being positioned for emitting laser light with intersecting laser beams with a laser beam intersection region in a region of the air flow path,
 a calculation and control unit designed for controlling an adjustment of laser intensities and allowing adjustment of an amplitude of each laser pulse using detected amplitudes of a previous pulse, and
 a first photodetector and a second photodetector positioned for the detection of laser light scattered in the laser beam intersection region by airborne particles contained in the laminar air flow,
 the first laser and the second laser being designed for emission of laser light of identical laser emission wavelength,
 the first laser and the second laser being designed for emission of time-amplitude modulated laser light with a phase shift between the laser beam of the first laser and the laser beam of the second laser, and
 the first photodetector and the second photodetector being positioned and designed each for the detection of scattered laser light from both the first laser and the second laser.

2. The measurement device according to claim 1, wherein the first laser and the second laser are positioned for emission of laser beams intersecting at an angle of approximately 90°.

3. The measurement device according to claim 1, wherein the first laser and the second laser are designed for emitting time-amplitude modulated laser light with a phase shift of approximately 90° between the laser beam of the first laser and the laser beam of the second laser.

4. The measurement device according to claim 1, wherein the first photodetector and the second photodetector are provided each with a narrow-band optical filter with a central transmission wavelength identical to the laser emission wavelength.

5. The measurement device according to claim 1, further comprising a calculation and control unit designed for correlation of signals of scattered laser light from the first photodetector and the second photodetector for determination of a size of airborne particles scattering the laser light and also for a determination of a location of detected airborne particles from a known intersection region of the laser beams.

6. The measurement device according to claim 1, further comprising an imaging detector, particularly a CCD or CMOS camera, designed and positioned for taking an image of a detected airborne particle after receiving an initiating trigger signal.

7. The measurement device according to claim 1, further comprising an imaging detector, particularly a CCD or CMOS camera, combined with a diverging lens positioned in an optical reception path, designed and positioned for taking an image of an airborne particle, after receiving an initiating trigger signal, for determination of a scattering pattern caused by the airborne particle.

8. The measurement device according to claim 1, further comprising a flash light source for emitting short-wavelength light, particularly ultra-violet light, designed and positioned for exciting fluorescence or phosphorescence from a detected airborne particle, and by the fact that it comprises a third photodetector, particularly a multi-anode photomultiplier or an intensified CCD camera, combined with an objective for fluorescence or phosphorescence light collection, and a spectrally resolving optical element positioned in an optical reception path for fluorescence or phosphorescence emitted by the airborne particle, designed and positioned for the detection of an optical spectrum of the fluorescence and/or phosphorescence emitted by the airborne particle.

9. A measurement method for the detection of airborne particles by a measurement device, comprising:
 a nozzle designed to produce a laminar flow of air with a flow path beyond the nozzle,
 a first laser and a second laser, the first laser and the second laser being positioned for emitting laser light with intersecting laser beams with a laser beam intersection region in a region of the air flow path,
 a first photodetector and a second photodetector positioned for the detection of laser light scattered in the laser beam intersection region by airborne particles contained in the laminar air flow, and
 a calculation and control unit designed for controlling an adjustment of laser intensities,
 the measurement method comprising the step of:
  producing with the nozzle a laminar flow of air potentially containing airborne particles to be detected,
  emitting laser light of identical wavelength from the first laser and the second laser, the first laser and the second laser being operated for emission of time-amplitude modulated laser light with a phase shift between the laser beam of the first laser and the laser beam of the second laser,
  detecting laser light scattered by an airborne particle located in a superposition region of the region of the air flow path with the intersection region of the laser beams from the first laser and the second laser both by the first photodetector and by the second photodetector, and
  controlling laser intensities of the first laser and the second laser by said calculation and control unit by adjusting an amplitude of each laser pulse using detected amplitudes for a previous pulse.

10. The measurement method according to claim 9, wherein the first laser and the second laser are positioned for emission of laser beams intersecting at an angle of approximately 90°.

11. The measurement method according to claim 9, wherein the first laser and the second laser are operated for emitting modulated laser light with a phase shift of approximately 90° between the laser beam of the first laser and the laser beam of the second laser.

12. The measurement method according to claim 9, wherein signals of scattered laser light from the first photodetector and the second photodetector are correlated by a calculation and control unit of the measurement device for determination of a size of airborne particles scattering the laser light and preferably also for determination of a location of detected airborne particles from a known intersection region of the laser beams.

13. Application of the method of claim 9 for determination of size and/or location of particles in a gas and/or determination of the family, respectively of the species of the detected particles.

14. Use of the measurement device according to claim 1 for determination of size and/or location of particles in a gas and/or determination of the family, respectively of the species of the detected particles.

\* \* \* \* \*